United States Patent [19]
Young

[11] 3,974,156
[45] Aug. 10, 1976

[54] 2-(SUBSTITUTED ANILINO) METHYLMORPHOLINE COMPOUNDS

[75] Inventor: Edwin Harry Paterson Young, Macclesfield, England

[73] Assignee: Imperial Chemical Industries Limited, London, England

[22] Filed: Aug. 10, 1973

[21] Appl. No.: 387,379

[30] Foreign Application Priority Data
Aug. 11, 1972 United Kingdom............... 37550/72

[52] U.S. Cl.......................... 260/247.1 R; 424/248; 260/247.1 E; 260/247.2 A; 260/247.5 R; 260/247.5 J
[51] Int. Cl.²...................................... C07D 295/12
[58] Field of Search.............. 260/247.5 R, 247.1 R, 260/247.2 A

[56] References Cited
FOREIGN PATENTS OR APPLICATIONS
940,035  10/1973  United Kingdom.............. 260/247.5

*Primary Examiner*—Henry R. Jiles
*Assistant Examiner*—R. W. Ramsuer
*Attorney, Agent, or Firm*—Cushman, Darby & Cushman

[57] ABSTRACT

The disclosure relates to new 2-(substituted anilino)-methylmorpholine derivatives which possess sedative activity, to processes for the manufacture of the said morpholine derivatives, and to pharmaceutical compositions containing them. Typical of the morpholine derivatives disclosed is 2-(3-methoxyanilino)methylmorpholine.

3 Claims, No Drawings

2-(SUBSTITUTED ANILINO) METHYLMORPHOLINE COMPOUNDS

This invention relates to novel morpholine derivatives which possess valuable sedative properties According to the invention there is provided a morpholine derivative of the formula:

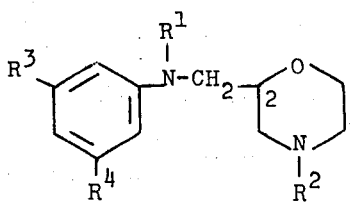

I wherein $R^1$ is hydrogen or an acyl radical of up to 4 carbon atoms; $R^2$ is hydrogen or an alkyl radical of 1 to 6 carbon atoms; $R^3$ is a halogen atom, an alkyl radical of 1 to 4 carbon atoms, a methoxy radical, a methylthio radical or a trifluoromethyl radical; and $R^4$ is hydrogen or a trifluoromethyl radical; and the pharmaceutically-acceptable acid-addition salts thereof.

It will be observed that the morpholine derivative of the invention possesses an asymmetric carbon atom, marked 2 in the above formula I, and that accordingly such a compound can be isolated in a racemic form and two optically-active forms. This specification is addressed to the racemic form of the compound of the formula I and to any optical isomer which exhibits the useful properties which are hereafter defined; it being a matter of common general knowledge how to resolve the racemic form and to determine the biological properties of the optical isomers.

A particularly suitable value for $R^1$ when it is an acyl radical is an acetyl radical.

A particularly suitable value for $R^2$ when it is an alkyl radical of 1 to 6 carbon atoms is a methyl, ethyl n-propyl or i-propyl radical.

A particularly suitable value for $R^3$ or $R_4$ when it is a halogen atom is a fluorine or chlorine atom.

A particularly suitable value for $R^3$ or $R^4$ when it is an alkyl radical of 1 to 4 carbon atoms is a methyl, ethyl, n-propyl or n-butyl radical.

A preferred group of compounds comprises those of formula I in which $R^1$, $R^2$ and $R^4$ are hydrogen and $R^3$ is a chlorine atom or a methoxy, methylthio or thrifluoromethyl radical.

A suitable acid-addition salt of the morpholine derivative of the invention is, for example, a hydrochloride, hydrobromide, phosphate or sulphate, or a citrate, acetate, oxalate, methanesulphonate, toluene-p-sulphonate, tartrate, maleate, gluconate or resinate.

The morpholine derivative of the invention may be manufactured by suitable modifications of well known methods, for example:

a. for a compound wherein $R^2$ is hydrogen, hydrogenolysis of a compound of the formula:

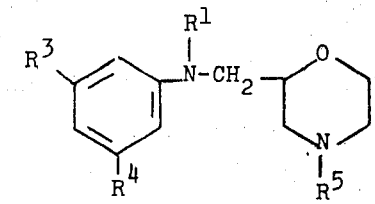

II or an acid addition salt thereof, wherein $R^1$, $R^3$ and $R^4$ have the meanings stated above and wherein $R^5$ is an α-arylalkyl radical of up to 11 carbon atoms.

The α-arylalkyl radical is preferably a benzyl radical and the hydrogenolysis is preferably carried out by means of hydrogen in the presence of a palladium on charcoal catalyst, in a diluent or solvent. The hydrogenolysis is conveniently carried out at ambient temperature and atmospheric pressure, and may be accelerated by the presence of an acidic catalyst, for example hydrochloric acid.

b. for a compound wherein $R^1$ is hydrogen, hydrolysis of a compound of the formula:

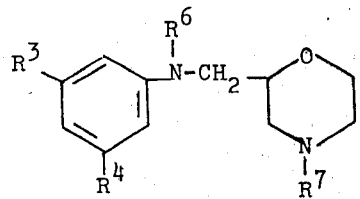

III wherein $R^3$ and $R^4$ have the meanings stated above, $R^6$ is hydrogen or an acyl radical of up to 11 carbon atoms and $R^7$ is hydrogen, an alkyl radical of 1 to 6 carbon atoms or an acyl radical of up to 11 carbon atoms, provided that when $R^6$ is hydrogen then $R^7$ is an acyl radical of up to 11 carbon atoms. The acyl radical of up to 11 carbon atoms may be an aryloxycarbonyl radical, for example a phenoxycarbonyl radical, or it may be an alkanoyl radical, for example an acetyl radical. The hydrolysis may be carried out with an acid, for example hydrochloric or sulphuric acid, or a base, for example sodium hydroxide or potassium hydroxide, in a diluent or solvent, for example water, an alcohol or aqueous alcohol, for example methanol or ethanol, or dimethylsulphoxide. The hydrolysis may be accelerated or completed by the application of heat, for example at 100°C. or at the boiling point of the solvent.

c. the reaction of a compound of the formula:

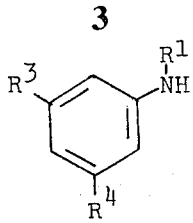

with a compound of the formula:

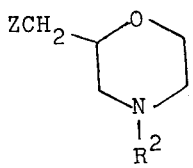

wherein $R^1$, $R^2$, $R^3$ and $R^4$ have the meanings stated above and wherein Z stands for a halogen atom, for example a chlorine or bromine atom, or for an alkane- or arene-sulphonyloxy radical, for example a methanesulphonyloxy or toluene-p-sulphonyloxy radical. The process may be carried out using the salt of a compound of the formula IV, made by reaction of the compound with a strong base, for example an alkali metal or an amide or hydride thereof, for example sodium hydride. The process may be carried out in a diluent or solvent, for example dimethylformamide, dimethylsulphoxide, dioxan or dimethoxyethane and it may be carried out at an elevated temperature, for example a temperature of up to 150°C.

d. for a compound in which $R^1$ is hydrogen, heating a compound of the formula:

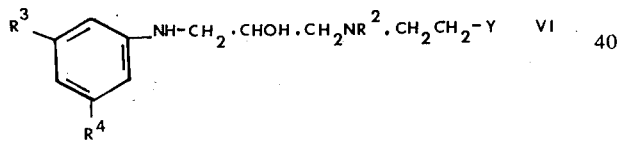

or an acid addition salt thereof, wherein $R^2$, $R^3$ and $R^4$ have the meanings stated above and wherein Y stands for a halogen atom, for example a chlorine or bromine atom, or for a sulphonyloxy radical, for example a radical of the formula $OSO_2OR^8$ wherein $R^8$ stands for hydrogen or for a lower alkyl or an aryl radical, for example the methyl, ethyl, phenyl or p-tolyl radical, with a base.

The process may be carried out in a diluent or solvent, for example water, an alcohol, for example methanol, ethanol, isopropanol, n-butanol, t-butanol or ethylene glycol, or an ether, for example diethyl ether, dimethoxyethane, tetrahydrofuran or dioxan, or a mixture of any of the abovementioned solvents; it may be carried out at ambient temperature or at a temperature up to the boiling point of the diluent or solvent, or at a temperature of between 40° and 100°C., and it may be carried out in the presence of an alkali or alkaline earth metal hydroxide, for example sodium, potassium or barium hydroxide.

The compound of the invention which is racemic may be resolved into its optically-active isomers by conventional methods. The resolution may be performed on the racemic compound itself or on racemic intermediates which are then used to manufacture the compound of the invention.

The starting material of the formula II for process (a) may be obtained by reaction of a compound of the formula IV with a compound of the formula:

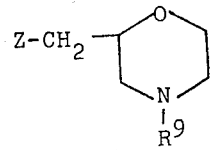

wherein $R^9$ is an α-arylalkyl radical.

The starting material of the formula III for use in process (b) may be prepared, for example, by reaction of 2-toluene-p-sulphonyloxymethylmorpholine, or its corresponding 4-acyl or 4-protected derivative, with a substituted aniline or N-acylaniline, followed by removal of the protecting group if necessary.

The starting material of the formula V in which $R^2$ is an alkyl radical of 1 to 6 carbon atoms may be prepared, for example, by reaction of allylglycidyl ether with an alkylamine followed by acylation of the product with chloracetyl chloride and subsequent ring closure to give the 2-allyloxymethyl-4-alkylmorpholine-5-one. This lactam is reduced with $LiAlH_4$, the allyl group is cleaved and the resulting alcohol reacted with toluene-p-sulphonyl chloride.

The starting material of the formula VI for use in process (d) may be prepared, for example, by reaction of an amine of the formula:

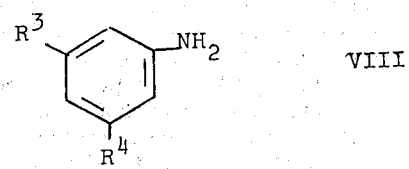

with epichlorhydrin, followed by reaction of the product with a compound of the formula $HNR^2.CH_2CH_2Y$.

The compounds of the invention possess sedative activity in warm-blooded animals as demonstrated by the reduction in spontaneous activity in mice as measured by photobeam interruption. This test is a standard one for the measurement of sedative activity (Riley and Spinks, *J. Pharm. Pharmacol.*, 1958, 10, 662–663) and clinically useful sedatives such as haloperidol and chlorpromazine are active on this test.

All the compounds exemplified in this specification are active in the reduction of spontaneous activity test at a dose of equal to or less than 30 mg./kg. in mice while at the same time showing no obvious signs of toxicity. The test is carried out as follows:

Groups of 6 mice are dosed orally with the compound under test and are immediately placed individually in cages provided with a central horizontal scanning photobeam. The number of beam interruptions in the first 45 minutes is recorded, and the percentage inhibition of movement relative to control animals is calculated. The compound is considered active if the amount of movement is reduced by more than one third compared to the control animals.

According to a further feature of the invention, there is provided a pharmaceutical composition which comprises as active ingredient a morpholine derivative of the invention in association with a non-toxic, pharmaceutically-acceptable diluent or carrier therefor.

The pharmaceutical composition may be, for example, in a form suitable for oral or parenteral administration, for which purposes it may be formulated by means known to the art into the form of, for example, tablets, capsules, aqueous or oily solutions or suspensions, emulsions, sterile injectable aqueous or oily solutions or suspensions, or dispersible powders.

The pharmaceutical composition of the invention may also contain, in addition to the morpholine derivative or salt thereof, one or more known drugs selected from neuroleptic-sedative agents, for example chlorpromazine, prochlorperazine, trifluoperazine and haloperidol; other sedative drugs and tranquillizers, for example chlordiazepoxide, phenobarbitone and amylobarbitone; β-adrenergic blocking agents, for example propranolol; drugs used in the treatment of Parkinson's disease, for example benzhexol; and antidepressant drugs, for example imipramine, desipramine, amitriptyline, nortriptyline, drugs of the amphetamine type and monoamineoxidase inhibitors, for example phenelzine and mebanazine.

A preferred pharmaceutical composition of the invention is one suitable for oral administration in unit dosage form, for example tablets and capsules, which contain between 20 and 200 mg. of active ingredient, or one suitable for intravenous or intramuscular injection, for example a sterile aqueous solution containing between 0.5 and 5% w/w of active ingredient.

When used to produce a sedative effect in warmblooded animals, a pharmaceutical composition of the invention may be administered to the host at such a dose that each host receives a total oral dose of between 3 and 30 mg./kg. of active ingredient per day or a total intravenous or intramuscular dose of between 0.5 and 5 mg./kg. per day, the composition being administered 2 to 4 times per day. Given to a man this is equivalent to a total oral dose of between 200 mg. and 2.0 g. of active ingredient per day or a total intravenous or intramuscular dose of between 40 and 400 mg. per day.

The invention is illustrated, but not limited, by the following Examples:

EXAMPLE 1

A solution of 4-benzyl-2-(3-methoxyanilino)methylmorpholine dihydrochloride monohydrate (2.0 g.) in methanol (50 ml.) is shaken in an atmosphere of hydrogen in the presence of 5% palladium/carbon catalyst until a molar equivalent of hydrogen has been absorbed. The solution is filtered, the methanol evaporated and the residue dissolved in water and the solution thus obtained is basified with dilute sodium hydroxide solution. The mixture is extracted with ether (3 × 100 ml.) and the ethereal solution is dried (MgSO₄), filtered and treated with an ethereal solution of oxalic acid. The precipitated oxalate is recrystallised from acetone to give 2-(3-methoxyanilino)methylmorpholine oxalate, m.p. 137°C.

The 4-benzyl-2-(3-methoxyanilino)methylmorpholine dihydrochloride monohydrate used as starting material may be prepared as follows:

A mixture of 3-methoxyaniline (12.5 g.) and 4-benzyl-2-toluene-p-sulphonyloxymethylmorpholine (18.6 g.) is stirred and heated on the steam bath (95°C.) under nitrogen for 24 hours. The mixture is cooled and ether added. The solid thus obtained is collected and crystallised from ethyl acetate to give 4-benzyl-2-(3-methoxyanilino)methylmorpholine toluene-p-sulphonate, m.p. 102–103°C. The toluene-p-sulphonate salt is converted into the corresponding dihydrochloride by basifying it with dilute sodium hydroxide solution, extracting the base into ether (3 × 200 ml.), washing the ethereal extract with water and then drying it over anhydrous magnesium sulphate followed by filtration and treatment of the ethereal solution of base with ethereal hydrochloric acid solution. The 4-benzyl-2-(3-methoxyanilino)methylmorpholine dihydrochloride monohydrate melts at 116–118°C. after crystallisation from methanol/ethyl acetate.

The 4-benzyl-2-toluene-p-sulphonyloxymethylmorpholine used as starting material may be obtained as follows:

To a solution of 4-benzyl-2-hydroxymethylmorpholine (118.8 g.) in dry pyridine (250 ml.) toluene-p-sulphonyl chloride (120.2 g.) is added gradually at 18°–25°C. The mixture is stirred for 20 hours at ambient temperature (ca. 20°C.) and the pyridine is removed under diminished pressure. The residue is diluted with water, the mixture made alkaline by the addition of sodium hydroxide solution, and the product is then extracted into ether. The ethereal solution is dried (MgSO₄) and filtered, the ether is evaporated and the residual solid is crystallised from cyclohexane or petroleum ether (b.p. 60°–80°C.) to give 4-benzyl-2-toluene-p-sulphonyloxymethylmorpholine, m.p. 78°–79°C.

EXAMPLE 2

The process described in the first part of Example 1 is repeated except that an equivalent amount of 4-benzyl-2-(3-trifluoromethylanilino)methylmorpholine dihydrochloride monohydrate is used in place of 4-benzyl-2-(3-methoxyanilino)methylmorpholine dihydrochloride monohydrate, and using water in place of methanol as solvent. There is thus obtained 2-(3-trifluoromethylanilino)methyl morpholine oxalate, m.p. 108°–110°C. on recrystallisation from methanol/ether.

The 4-benzyl-2-(3-trifluoromethylanilino)methylmorpholine dihydrochloride monohydrate used as starting material may be obtained by repeating the process described in the second part of Example 1 using an equivalent amount of 3-trifluoromethylaniline as starting material in place of 3-methoxyaniline. There is thus obtained 4-benzyl-2-(3-trifluoromethylanilino)methylmorpholine dihydrochloride monohydrate, m.p. 141°C. on recrystallisation from methanol/ethyl acetate.

EXAMPLE 3

The process described in the first part of Example 1 is repeated except that the appropriate N-benzyl anilinomethylmorpholine salt is used as starting material in place of 4-benzyl-2-(3-methoxyanilino)methylmorpholine dihydrochloride. The following compounds are thus obtained.

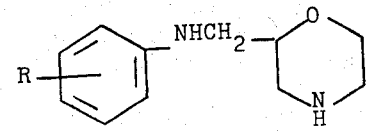

| R | Reaction Solvent | Salt | m.p. (°C.) | Recrystallisation Solvent |
|---|---|---|---|---|
| 3-n-butyl | ethanol | oxalate | 124–126 | water |
| 3,5-di-CF$_3$ | water/ ethanol | dihydro- chloride | 153–165 | acetone/ ether |

The starting materials used in the above process may be obtained by repeating the process described in the second part of Example 1 using an equivalent amount of the appropriate substituted aniline in place of 3-methoxyaniline. The following compounds are thus obtained:

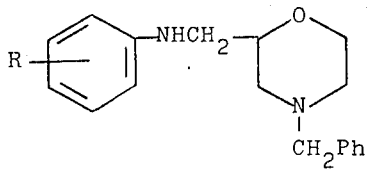

| R | Salt | m.p. (°C.) | Recrystallisation Solvent |
|---|---|---|---|
| 3-n-butyl | toluene-p-sulphonate | 140–142 | ethyl acetate |
| 3,5-di-CF$_3$ | dihydrochloride | 201–204 | methanol/ether |

EXAMPLE 4

To a solution of 4-benzyl-2-(3-methylthioanilino)methylmorpholine (1.7 g.) in toluene (50 ml.) is added hexamethylphosphoramide (1 ml.) and then phenyl chloroformate (1.5 ml.). The mixture is heated under reflux for 18 hours, the toluene is then removed under reduced pressure, the oily residue is dissolved in ether and the ethereal solution is washed successively with sodium hydroxide solution, water, hydrochloric acid and water before drying over anhydrous magnesium sulphate. Evaporation of the dried filtered ethereal solution gives yellow oil (2.4 g.) or 2-(3-methylthioanilino)methyl-4-phenoxycarbonylmorpholine, which is dissolved in dimethylsulphoxide (20 ml.) and this solution is added to a solution of sodium methylsulphinylmethide [prepared in the usual way from sodium hydride (2.4 g.) and dimethylsulphoxide (50 ml.) ]. Water (1.8 ml.) is then added when the temperature of the mixture rises to about 60°C. The solution is stirred for 1 hour and then poured into water containing ice and the mixture extracted with ether (3 × 100 ml.). The ethereal solution is washed with water, dried (MgSO$_4$) and filtered and the filtrate is treated with an ethereal solution of oxalic acid to precipitate 2-(3-methylthioanilino)methylmorpholine oxalate, m.p. 114°–115°C. after recrystallisation from acetone.

The above process is repeated using an equivalent amount of 4-benzyl-2-(3-chloroanilino)methylmorpholine in place of 4-benzyl-2-(3-methylthioanilino)methylmorpholine, and there is thus obtained 2-(3-chloroanilino)methylmorpholine oxalate, m.p. 125°–127°C. on recrystallisation from methanol/ether.

The starting materials for the above processes may be prepared by repeating the process described in the second part of Example 1, using equivalent amounts of 3-methylthioaniline and 3-chloroaniline in place of 3-methoxyaniline. There are thus obtained 4-benzyl-2-(3-methylthioanilino)methylmorpholine toluene-p-sulphonate, m.p. 98°–101°C. on recrystallisation from ethyl acetate, and 4-benzyl-2-(3-chloroanilino)methylmorpholine dihydrochloride, m.p. 150°–153°C. on recrystallisation from methanol/ether, respectively, from which the free bases may be prepared in the usual manner.

EXAMPLE 5

A mixture of 3-trifluoromethylaniline (5.6 g.) and 4-n-propyl-2-toluene-p-sulphonyloxymethylmorpholine (10 g.) is heated at 200°C. under an atmosphere of nitrogen for 4 hours. The resulting black tar is cooled, stirred with dilute sodium hydroxide solution and extracted with ether. The ethereal extract is dried, filtered, and the filtrate is treated with an ethereal solution of hydrochloric acid to give a sticky solid which solidifies on addition of acetone. Crystallisation of the solid from ethanol/ether gives 4-n-propyl-2-(3-trifluoromethylanilino)methylmorpholine dihydrochloride, m.p. 168°–172°C. The 4-n-propyl-2-toluene-p-sulphonyloxymethylmorpholine used as starting material may be obtained as follows:

Allylglycidyl ether (94.7 g.) is added with stirring to a solution of n-propylamine (98 g., 137 ml.) in ethanol (200 ml.). The mixture is heated under reflux for 18 hours and the solvent and excess of n-propylamine are distilled off. The residual oil is distilled and the fraction b.p. 79°–85°C. at 1 m.m. is collected to give 1-allyloxy-3-n-propylamino-2-propanol.

A solution of 1-allyloxy-3-n-propylamino-2-propanol (95.2 g.) in a mixture of dry methylene chloride (275ml.) and triethylamine (80 ml.) is cooled to between −5° and 0°C. and a solution of chloroacetylchloride (42 ml.) in methylene chloride (60 ml.) is added dropwise with stirring during 2 hours. The mixture is allowed to warm to ambient temperature (18°–20°C.) and stirred at this temperature for 18 hours. The solution is washed with 2N hydrochloric acid (2 × 100 ml.) and then with water (100 ml.) and dried (MgSO$_4$). Removal of the solvent under reduced pressure gives N-(3-allyloxy-2-hydroxypropyl)-N-n-propyl-α-cloroacetamide (119.7 g.) as an oil which is used without further purification.

A solution on N-(3-allyloxy-2-hydroxypropyl)-N-n-propyl-α-chloroacetamide (119.7 g.) in methanol is added to a solution of sodium methoxide prepared by dissolving sodium (13 g.) in methanol (900 ml.). The mixture is stirred and heated under reflux for 18 hours and the solvent is then distilled off. Water (400 ml.) is added to the residue and the resulting mixture is extracted with ethyl acetate (1 × 400 ml.; 2 × 200 ml.). The combined extracts are washed with water, dried (MgSO$_4$), filtered and the filtrate is evaporated. The residual oil is distilled and the fraction b.p. 123°–125°C. at 0.7 m.m. is collected. There is thus obtained 2-allyloxymethyl-4-n-propylmorpholin-5-one (65.2 g.).

A solution of 2-allyloxymethyl-4-n-propylmorpholin-5-one (65 g.) in dry ether (100 ml.) is added slowly with stirring to a suspension of lithium aluminium hydride (17.5 g.) in dry ether (700 ml.). The rate of addition is adjusted so that the reaction mixture refluxes gently. When the addition is complete the reaction mixture is stirred at ambient temperature (18°–20°C.) for 18 hours and then water (90 ml.) is added very carefully dropwise to decompose the complex and excess of lithium aluminium hydride. The ethereal solution is filtered and the solid residue is washed with ether. The filtrate and ethereal washings are combined, dried (Na$_2$SO$_4$), filtered and the ether evaporated. The product, 2-allyloxymethyl-4-n-propylmorpholine is obtained as an oil b.p. 80°–90°C. at 1 m.m. which forms a hydrogen oxalate, m.p. 125°–127°C.

2-Allyloxymethyl-4-n-propylmorpholine (59.7 g.) is heated under reflux in hydrochloric acid (240 ml., 20%) for 18 hours. The solution is cooled, diluted with ice and water, and basified with sodium hydroxide and extracted with ether (3 × 200 ml.). The ethereal solution is dried (MgSO$_4$) filtered and the ether evaporated to give recovered starting material. The aqueous layer is concentrated to a small volume and precipitated salt is removed by filtration and washed with ether. The filtrate is extracted with ether (3 × 100 ml.) and the combined extracts and ethereal wash are dried (MgSO$_4$) filtered and the ether evaporated. 2-Hydroxymethyl-4-n-propylmorpholine (16.7 g.) is obtained as a viscous oil which forms a hydrogen oxalate, m.p. 133°–135°C. after crystallisation from a methanol/ether mixture.

2-Hydroxymethyl-4-n-propylmorpholine (16.2 g.) is dissolved in dry pyridine (50 ml.) and a solution of toluene-p-sulphonylchloride (21.4 g.) in dry pyridine (50 ml.) is added dropwise with stirring. The mixture is stirred at 20°–≅°C. for 3 hours. The pyridine is removed under reduced pressure, water (100 ml.) is added to the residue and the product is extracted into ether (3 × 150 ml.). The ethereal solution is washed with water, dried (MgSO$_4$), filtered and the ether evaporated to give 4-n-propyl-2-toluene-p-sulphonyloxymethylmorpholine (30.6 g.) as an oil which forms a hydrochloride, m.p. 172°–173°C. on recrystallisation from methanol/ether.

EXAMPLE 6

A solution of 4-benzyl-2-(N-acetyl-3-methoxyanilino)methylmorpholine oxalate (9 g.) in a mixture of ethanol (100 ml.) and water (10 ml.) is shaken in an atmosphere of hydrogen with palladium on carbon catalyst (0.5 g.; 5%) until no more hydrogen is absorbed. The catalyst is then filtered off and from the filtrate on chilling and standing 2-(N-acetyl-3-methoxyanilino)methylmorpholine oxalate, m.p. 175°–176°C. (decomposition) is obtained.

The 4-benzyl-2-(N-acetyl-3-methoxyanilino)methylmorpholine oxalate used as starting material may be obtained as follows:

4-Benzyl-2-(3-methoxyanilino)methylmorpholine (13.4) (obtained from the dihydrochloride monohydrate salt whose preparation is described in Example 1) is heated in acetic anhydride (25 ml.) for 3 hours at 95°–100°C. The reaction mixture is cooled and poured into ice and water (500 g.), then basified with sodium hydroxide solution and extracted with ether (2 × 250 ml.). The ethereal solution is dried over anhydrous magnesium sulphate, filtered and an ethereal solution of oxalic acid is added. The precipitated solid (19.6 g.) is collected and recrystallised from methanol/ethyl acetate to give 4-benzyl-2-(N-acetyl-3-methoxyanilino)-methylmorpholine oxalate, m.p. 159°–160°C. (decomposition).

EXAMPLE 7

A mixture of 2-(N-acetyl-3-methoxyanilino)methylmorpholine oxalate (2 g.) and concentrated hydrochloric acid (25 ml.) is heated under reflux for 24 hours. The solution is cooled, diluted with ice (25 g.) basified with sodium hydroxide solution and then extracted with ether (2 × 100 ml.). The ethereal extract is dried over anhydrous sodium sulphate, filtered and concentrated to about 25 ml. On addition of an ethereal solution of oxalic acid there is obtained 2-(3-methoxyanilino)methylmorpholine oxalate, m.p. 156°–157°C. The corresponding maleate at 145°–147°C. (decomposition).

What we claim is:

1. A morpholine selected from compounds of the formula:

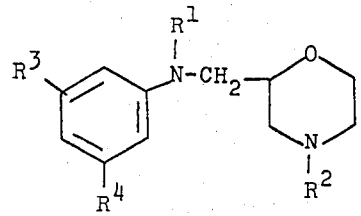

wherein R$^1$ is hydrogen or acetyl of up to 4 carbon atoms; R$^2$ is hydrogen or alkyl of 1 to 6 carbon atoms; R$^3$ is halogen, alkyl of 1 to 4 carbon atoms, methoxy, methylthio or trifluoromethyl; and R$^4$ is hydrogen or trifluoromethyl; and the non-toxic, pharmaceutically acceptable acid-addition salts thereof.

2. A morpholine as claimed in claim 1 wherein R$^1$ is hydrogen or accetyl; R$^2$ is hydrogen or methyl, ethyl, n-propyl or i-propyl; R$^3$ is fluorine, chlorine, methyl, ethyl, n-propyl, n-butyl, methoxy, methylthio or trifluoromethyl and R$^4$ is hydrogen or trifluoromethyl.

3. A morpholine as claimed in claim 1 selected from the group consisting of 2-(3-chloroanilino)methylmorpholine, 2-(3-methoxyanilino)methylmorpholine, 2-(3-methylthioanilino)methylmorpholine and 2-(3-trifluoromethylanilino)methylmorpholine.

* * * * *